US007057055B2

(12) United States Patent
Bergman et al.

(10) Patent No.: US 7,057,055 B2
(45) Date of Patent: Jun. 6, 2006

(54) PROCESS FOR PREPARING A DEUTERATED OR TRITIATED COMPOUND

(75) Inventors: Robert C. Bergman, Kensington, CA (US); Steven R. Klei, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 11/243,852

(22) Filed: Oct. 4, 2005

(65) Prior Publication Data

US 2006/0036103 A1 Feb. 16, 2006

Related U.S. Application Data

(62) Division of application No. 10/854,375, filed on May 25, 2004, which is a division of application No. 10/103,481, filed on Mar. 21, 2002.

(60) Provisional application No. 60/278,283, filed on Mar. 22, 2001, now Pat. No. 6,794,522.

(51) Int. Cl.
*C07D 307/36* (2006.01)
*C07C 63/06* (2006.01)
*C07C 41/18* (2006.01)
*C07C 29/00* (2006.01)

(52) U.S. Cl. .................. 549/429; 562/493; 568/671; 568/840

(58) Field of Classification Search ................ 549/429; 562/493; 568/671, 840
See application file for complete search history.

(56) References Cited

U.S. PATENT DOCUMENTS

| | | | |
|---|---|---|---|
| 3,510,519 A | 5/1970 | Frejaville et al. | |
| 3,900,557 A | 8/1975 | Strathdee | |
| 3,966,781 A * | 6/1976 | Atkinson et al. | ........... 554/161 |
| 3,989,705 A | 11/1976 | Werstiuk et al. | |
| 4,421,865 A | 12/1983 | Shen | |
| 4,874,890 A * | 10/1989 | Kato et al. | ................. 560/256 |
| 5,149,820 A | 9/1992 | Borretzen et al. | |
| 5,186,868 A | 2/1993 | Andres et al. | |
| 5,733,984 A | 3/1998 | Nakahara et al. | |
| 5,830,763 A | 11/1998 | Junk et al. | |

FOREIGN PATENT DOCUMENTS

| | | | |
|---|---|---|---|
| EP | 276675 A2 * | 8/1988 | |
| JP | 63030447 A * | 2/1988 | |

OTHER PUBLICATIONS

Yoshida et al., Activation of Water Molecule. 2 . . . Platinum (0) Phosphine Complexes and the Applications as Catalysts for H-D Exchange and Hydration Reactions, Journal of the American Chemical Society, vol. 101, No. 8, Apr. 11, 1977. pp. 2027-2038.*

Anderson et al., Homogenous Catalysis of Hydrogen-Deuterium Exchange Reactions Involving Cyclopentadienyl Complexes of Palladium and Platinum, Organometallics, vol. 2, No. 6, Jun. 1983, pp. 780-782.*

Hesk et al., "Deuteration of Acetanilides and Other Substituted Aromatics Using [Ir(COD)(Cy3P)(Py)]PF6 as Catalyst," Journal of Labelled Compounds and Radiopharmaceuticals, vol. 36 ( No. 5), p. 497-502, (Mar. 7, 1995).

Heys et al., "Deuterium Exchange Labelling of Substituted Aromatics Using [IrH2(Me2CO)2(PPh3)2]BF4," Journal of Labelled Compounds and Radiopharmaceuticals, vol. 33 ( No. 5), p. 431-438, (1993).

Adair, "Synthesis and Thermolysis of Carbonyl Cyclopentadienyl Diyhdridoiridium and Dicarbonyl Cyclopentadienyl Dihydridorhenium," Dissertation Abstracts International, vol. 41 ( No. 11B), p. 4108, (1980).

Krutii et al., "Catalysis by Ruthenium and Rhodium Triphenylphosphine Complexes of the Exchange of Deuterium in the Oxygen-Deuterium Group of Octadeutero-2-Propanol in Water," Zhumal Organicheoskoi Khimii, vol. 12 ( No. 4), p. 748-750, (1976).

Shu et al., "Direct Tritium Labeling of Multifunctional Compounds using Organoiridium Catalysis. 2.," Journal of Labelled Compounds and Radiopharmaceuticals, p. 797-807, (Mar. 12, 1999).

Stang et al., "Synthesis, Characterization, and Reaction Chemistry of New Trifluoromethanesulfonato Complexes of Rhodium and Iridium: Formation of Cationic Rh-Pt and Ir-Pt Heterobinuclear Complexes with Bridging Chloride Ligands," Organometallics, vol. 11 ( No. 1), p. 231-237, (1992).

Glueck et al., "Monomeric (Pentamethylcyclopentadienyl)iridium Imido Compounds: Synthesis, Structure, and Reactivity," Journal of the American Chemical Society, vol. 113 ( No. 6), p. 2041-2054, (1991).

White et al., "(n5-Pentamethylcyclopentadienyl)Rhodium and -Iridium Compounds," Transition Metal Organometallics and Ligands, p. 228-234, (1992).

Oldham et al., "Synthesis and Characterization of Hydrotis(pyrazolyl)borate Dihydrogen/Hydride Complexes of Rhodium and Iridium," Journal of the American Chemical Society, vol. 119 ( No. 45), p. 11028-11036, (1997).

(Continued)

*Primary Examiner*—Rosalynd Keys
(74) *Attorney, Agent, or Firm*—Lawrence Berkeley National Laboratory

(57) ABSTRACT

A process for labeling organic compounds with deuterium and tritium is described using specific catalysts.

7 Claims, No Drawings

OTHER PUBLICATIONS

Isobe et al., "Pentamethylcyclopentadienyl-rhodium and -iridium complexes. Part 30.1 Trimethylphosphine-chloro-,-acetato-, and -hydrido-complexes and Related Compounds of (Hexamethylbenzene)ruthenium," Department of Chemistry, The University, J.C.S. Dalton (Sheffield), p. 2003-2008, (1981).

Klei et al., "Iridium-Catalyzed H/D Exchange into Organic Compounds in Water," Journal of the American Chemical Society, vol. 124 ( No. 10), p. 2092-2093, (2002).

Lenges et al., "Hydrogen/Deuterium Exchange Reactions and Transfer Hydrogenations Catalyzed by [C5Me5Rh(olefin)2] Complexes: Conversion of Alkoxysilanes to Silyl Enolates," Journal of the American Chemical Society, vol. 121 ( No. 18), p. 4385-4396, (1999).

Klei et al., "Iridium (III) and Rhodium (III) Complexes Bearing Chelating Cyclopentadienyl-Phosphine Ligands as C-H Activation Catalysts for the Deuteration of Hydrocarbons in D2O," Organometallics, vol. 21 ( No. 23), p. 4905-4911, (2002).

Klei et al., "Stoichiometric and Catalytic Behavior of Cationic Silyl and Silylene Complexes," Organometallics, vol. 21 ( No. 22), p. 4648-4661, (2002).

Klei et al., "Reactions of Cp*(PMe3)Ir(Me)OTf with Silanes: Role of Base-Free Silylene Complexes in Rearrangements of the Resulting Silicon-Based Ligands," Organometallics, vol. 21 ( No. 16), p. 3376-3387, (2002).

Tan et al., "Intermolecular Coupling of Isomerizable Alkenes to Heterocycles via Rhodium-Catalyzed C-H Bond Activation," Journal of the American Chemical Society, vol. 124 ( No. 47), p. 13964-13965, (2002).

Taw et al., "Carbon-Carbon Bond Activation of R-CN (R = Me, Ar, iPr, tBu) Using a Cationic Rh(III) Complex," Journal of the American Chemical Society, vol. 124 ( No. 16), p. 4192-4193, (2002).

Tan et al., "Intermediacy of an N-Heterocyclic Carbene Complex in the Catalytic C-H Activation of a Substituted Benzimidazole," Journal of the American Chemical Society, vol. 124 ( No. 13), p. 3202-3203, (2002).

Taw et al., "Synthesis and Investigation of [Cp*(PMe3)Rh(H)(H2)]+ and Its Partially Deuterated and Tritiated Isotopomers: Evidence for a Hydride/Dihydrogen Structure," Journal of the American Chemical Society, vol. 124 ( No. 18), p. 5100-5108, (2002).

Tellers et al., "Electronic and Medium Effects on the Rate of Amen C-H Bond Activation by Cationic Ir(III) Complexes," Journal of the American Chemical Society, vol. 124 ( No. 7), p. 1400-1410, (2002).

Tellers et al., "An Examination of C-H Bond Activation by Cationic Tpme2Ir(III) Complexes," Organometallics, vol. 20 ( No. 23), p. 4819-4832, (2001).

Klei et al., "Cationic Ir(III) Alkyl and Hydride Complexes: Stoichiometric and Catalytic C-H Activation by Cp*(PMe3)Ir(R)(X) in Homogeneous Solution," Journal of Molecular Catalysis A: Chemical, p. 79-94, (2002).

Gerisch et al., "Rhodium(III) and Rhodium(II) Complexes of Novel Bis(oxazoline) Pincer Ligands," Organometallics, vol. 22 ( No. 1), p. 47-58, (2003).

Regen, "Ruthenium-Catalyzed Hydrogen-Deuterium Exchange in Alcohols. A Convenient Method for Deuterium Labeling of Primary Alcohols", Jan. 1974, J. Org. Chem. vol. 39, No. 2, pp. 260-261.

Tsou et al., "Mechanism of Ruthenium-Catalyzed Linear Dimerization of Acrylonitrile: A Deuterium Labelling Study", Nov. 1983, J. of Molecular Catalysis, vol. 22, No. 1, pp. 29-45.

Gerogoullis et al., "Unambiguous Mono Deuterium Labelling of Alkyl Ethyl Ketones. . .of the Ethyl Group by Ruthenium (III) Catalyzed Isomerization of O-Deuterated Allylic Alcohols", Sep. 1984, Synthetic Communications, vol. 14, No. 11, pp. 1043-1046.

* cited by examiner

PROCESS FOR PREPARING A DEUTERATED OR TRITIATED COMPOUND

RELATED APPLICATIONS

This application is related to U.S. Ser. No. 60/278,283, filed Mar. 22, 2001, and is a divisional application of copending U.S. Ser. No. 10/854,375, filed May 25, 2004, which is a divisional application of U.S. Ser. No. 10/103,481, filed Mar. 21, 2002, now U.S. Pat. No. 6,794,522, the contents of all of which are hereby incorporated by reference in their entirety.

STATEMENT REGARDING FEDERALLY SPONSORED RESEARCH OR DEVELOPMENT

This invention was made with U.S. Government support under Grant (Contract) No. DE AC02-05CH11231 awarded by The U.S. Department of Energy for the operation of Ernest. Orlando Lawrence Berkeley National Laboratory. The U.S. Government has certain rights to this invention.

BACKGROUND OF THE INVENTION

Deuterium-labeled and tritium-labeled organic and organometallic compounds are used widely in spectroscopic experiments and in studies aimed at the elucidation of chemical structure and reaction mechanisms. These materials are expensive because they must be prepared by H/D exchange from unlabeled starting materials, often in multi-sequence procedures that require a more common compound to serve as a source of deuterium that can be transferred into the molecule of interest. Using classical methods it is usually easiest to exchange deuterium with so-called "activated" protons (e.g., protons that are acidic, or susceptible to electrophilic exchange using strong acids); exchange with "unactivated" protons is much more difficult. As a result, many deuterium-labeled compounds are either expensive or not available commercially. The present invention relates to a process for the preparation of a deuterated and/or tritiated compound which is useful as a raw material for pharmaceuticals, agricultural chemical, functional materials, analytical tracers and similar uses. When reference is made to deuterium and deuteration it is intended to include also tritium and tritiation, or a mixture of deuterium and tritium.

To make deuterium-labeled and tritium labeled organic and organometallic materials less expensively and more readily available, the chemical community requires a universal (preferably catalytic) method that would allow H/D exchange from an inexpensive deuterium and tritium source into a wide range of proton-containing compounds. The deuterium and tritium source that fits these criteria ideally is $D_2O$ and $T_2O$, due to their low cost and low toxicity.

REVIEW OF THE PRIOR ART

U.S. Pat. No. 3,510,519 to Frejaville et al. relates to the preparation of deuterated compounds by contacting and reacting under non-turbulent countercurrent flow conditions two compounds wherein one of the compounds is in liquid form and the other is in gaseous form. Frejaville et al. rely on a greatly elongated uncatalyzed reaction zone to achieve H-D exchange.

U.S. Pat. No. 3,989,705 describes a process for the deuteriation of organic substrates by hydrogen substitution using a strong acid and high temperatures.

U.S. Pat. No. 3,900,557 to Strathdee describes a catalyst comprising a transition metal coordination complex anchored on a cross-linked polystyrene. The anchored catalyst is useful for promoting H-D exchange between deuterated forms of hydrogen-containing gas streams and liquid water or alcohols.

U.S. Pat. No. 4,421,865 describes a process for deuterating compounds using a porous ion exchange resin.

U.S. Pat. No. 5,149,820 describes deuterated aromatic aldehydes used for anti-cancer drugs.

U.S. Pat. No. 5,186,868 describes methods for tritium labeling comprising reacting an organic solvented solution of alkali metal alkyl with a tritium gas in the presence of an alkyl tertiary amine.

U.S. Pat. No. 5,733,984 describes a process for the preparation of a deuterated compound comprising treating an organic compound in heavy water under high-temperature and high-pressure conditions not less than the subcritical temperature and subcritical pressure.

U.S. Pat. No. 5,830,763 describes a process for producing a deuterated compound comprising heating a deuterium oxide solution at a specific pH and at a temperature and pressure so that a supercritical reaction mass forms.

The above U.S. patents are hereby incorporated by reference in their entirety.

BRIEF SUMMARY OF THE INVENTION

In an important step toward the solution of the problems described in the paragraphs above, the inventors have surprisingly discovered a class of transition metal catalysts that catalyze the exchange of deuterium from $D_2O$ into a wide range of organic and organometallic compounds that are otherwise difficult to deuterate. Exchange occurs with both traditionally "activated" and "unactivated" hydrogens. The most active catalysts of this invention have been found to be [Cp*(PMe$_3$)IrH$_3$][OTf] and Cp*(PMe$_3$)IrCl$_2$, but this invention contemplates that any organometallic catalyst having the general formula described herein below is suitable. The latter catalyst is air stable, and is prepared in two high-yielding steps from commercially available IrCl$_3$-3H$_2$O.

The preparative advantages of these catalysts include their facile removal from products and their stability toward air and water. In contrast to related catalysts based on platinum that have been reported to act similarly, the use of strongly acidic conditions is not necessary, and their activity is higher than that of previously reported rhodium and iridium complexes. The H/D exchange according to the instant invention occurs under moderate conditions. Water typically participates in H/D exchange only with activated hydrogens, which would lead one to believe that the instant invention would not work efficiently; surprisingly the inventors have found two catalyst compositions that do work. Water often causes organometallic compounds to decompose, which would also lead one to believe that the instant invention would not work efficiently. Again however, the inventors have surprisingly found catalyst compositions that will work in an aqueous environment.

DETAILED DESCRIPTION OF THE PREFERRED EMBODIMENTS

The structures of the transition metal complexes that serve as catalysts in the deuteration or tritiation exchange process according to the instant invention are described below. The structures of a type of catalyst of this invention are shown below along with the example structures for Cp*(PMe$_3$)

IrCl₂ and [Cp*(PMe₃)IrH₃][OTf], which are two species shown to have good activity for hydrogen/deuterium and hydrogen/tritium exchange.

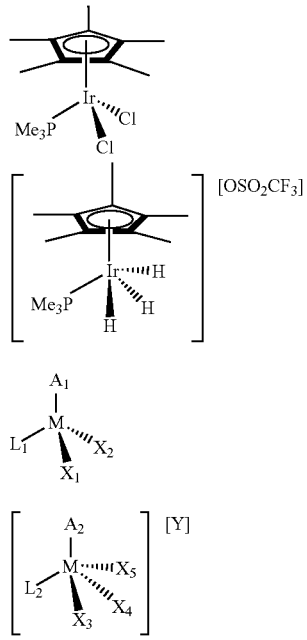

type I type II

A₁ and A₂ are meant to represent any ligand that can donate 6 electrons in the ionic counting scheme (described below, also known as the ionic model). A₁ and A₂ may also independently represent two groups that are fused, linked or bonded together and together the resultant combination of the two contribute six electrons, for example an allyl and alkene. L₁ and L₂ are meant to represent a two-electron donor in the ionic counting scheme. Non-limiting examples of ligands that function adequately for A₁ and A₂ include cyclopentadienide, pentamethylcyclopentadienide, (η⁵:η¹-(Me₂P(CH₂SiMe₂)C₅Me₄) and hydridotris(3,5-dimethylpyrazolyl)borate. L₁ and L₂ can be a trimethylphosphine, triphenylphosphine, tertbutylisonitrile, NH₂tBu, OH₂ or PF₃. X₁, X₂, X₃, X₄ and X₅ are independently or the same, and are meant to represent a two electron donor in the ionic counting scheme, which include species of Cl, Br, H, CH₂Cl₂ and OTf. M is a transition metal chosen from the group consisting of Co, Rh and Ir. Preferred is Ir. Y is an anion capable of rendering the compound charge neutral. Non limiting examples include OTf, B(C₆F₅)₃Me, NO₃, ClO₄, SbF₆, BPh₄, AlCl₄. Cp* is substituted cyclopentadienide, Me₃ is trimethyl and OTf is OSO₂CF₃. In this specification, tBu stands for a tert-butyl group, Ph stands for a phenyl group, which may be substituted or unsubstituted and Me stands for methyl. Cp stands for cyclopentadienide and the cyclopentadienide ring may be substituted or unsubstituted. It is contemplated that substitution may occur independently at each position of the ring. Substitution moieties include an alkyl group of 1–20 carbon atoms, such as 1–5 methyl groups, for example pentamethylcyclopentadienyl, hydrogen atoms, halogen atoms, substituted or unsubstituted aryl groups, a substituted or unsubstituted silyl group, an alkoxy group, an aryloxy group or a substituted or an unsubstituted amino group.

In another embodiment of the invention it is contemplated that the structure of the transition metal complex that serves as a catalyst in the deuteration or tritiation exchange process is as shown below:

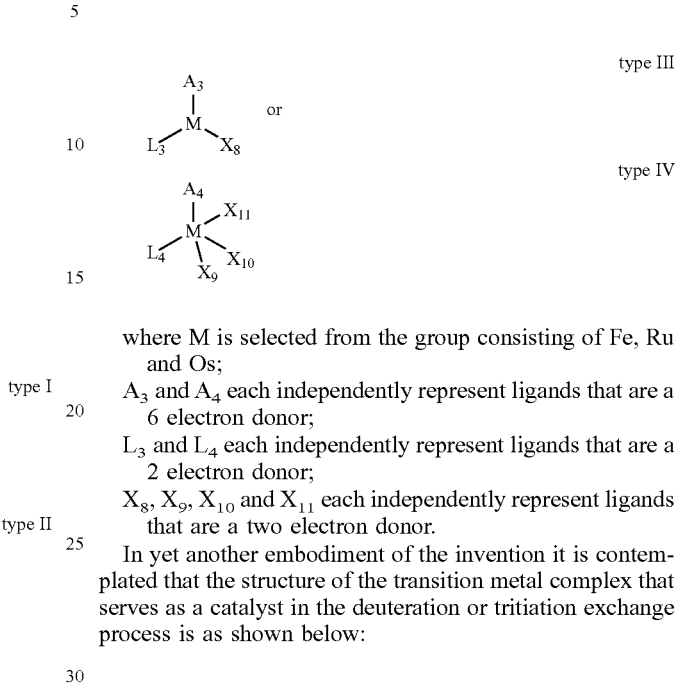

type III type IV where M is selected from the group consisting of Fe, Ru and Os;
A₃ and A₄ each independently represent ligands that are a 6 electron donor;
L₃ and L₄ each independently represent ligands that are a 2 electron donor;
X₈, X₉, X₁₀ and X₁₁ each independently represent ligands that are a two electron donor.

In yet another embodiment of the invention it is contemplated that the structure of the transition metal complex that serves as a catalyst in the deuteration or tritiation exchange process is as shown below:

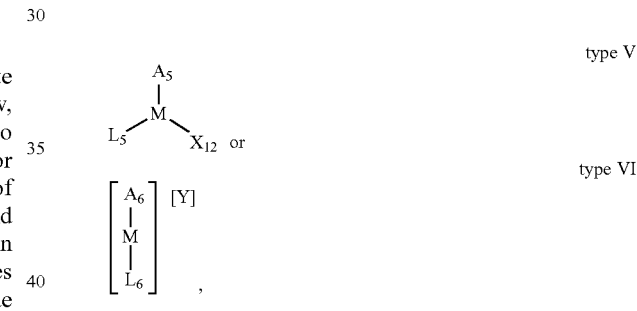

type V type VI where M is selected from the group consisting of Ni, Pd and Pt;
A₅ and A₆ each independently represent ligands that are a 6 electron donor;
L₅ and L₆ each independently represent ligands that are a 2 electron donor;
X₁₂ represents ligands that are a two electron donor;
and Y is an anion capable of creating a charge neutral complex.

For the type III–VI catalysts described above, A₃₋₆ are meant to represent any ligand that can donate 6 electrons in the ionic counting scheme (described below, also known as the ionic model). A₃₋₆ may also independently represent two groups that are fused, linked or bonded together and together the resultant combination of the two contribute six electrons, for example an allyl and alkene. L₃₋₆ are meant to represent a two-electron donor in the ionic counting scheme. Non-limiting examples of ligands that function adequately for A₃₋₆ include cyclopentadienide, pentamethylcyclopentadienide, (η⁵:η¹-(Me₂P(CH₂SiMe₂)C₅Me₄) and hydridotris(3,5-dimethylpyrazolyl)borate. L₃₋₆ can be a trimethylphosphine, triphenylphosphine, tertbutylisonitrile, NH₂tBu, OH₂ or PF₃. X₈₋₁₂ are independently or the same and are meant to represent a two electron donor in the ionic counting scheme, which include species of Cl, Br, H, CH₂Cl₂ and OTf. M is a transition metal chosen from the group consisting of Fe, Ru and Os for the type III and IV catalyst and from the group consisting of Ni, Pd and Pt for the type V and type VI catalyst. Y is an anion capable of rendering the compound charge neutral. This may be OTf, $B(C_6F_5)_3Me$, $NO_3$, $ClO_4$, $SbF_6$, $BPh_4$, $AlCl_4$. Cp* is substituted cyclopentadienide, $Me_3$ is trimethyl and OTf is $OSO_2CF_3$. Cp stands for cyclopentadienide and the cyclopentadienide ring may be substituted or unsubstituted. It is contemplated that substitution may occur independently at each position of the ring. Substitution moieties include an alkyl group of 1–20 carbon atoms, such as 1–5 methyl groups, for example pentamethylcyclopentadienyl, hydrogen atoms, halogen atoms, substituted or unsubstituted aryl groups, a substituted or unsubstituted silyl group, an alkoxy group, an aryloxy group or a substituted or an unsubstituted amino group.

When reference is made to deuterium and deuteration it is intended to include also tritium and tritiation, or a mixture of deuterium and tritium. This means that the catalysts described herein are useful for both deuteriation and tritiation.

When reference is made to moderate conditions, these are generally described in the art as pH neutral and a temperature of less than about 200° C.

When reference is made to organic substrate, it is meant any composition containing carbon capable undergoing deuteration or tritiation.

When reference is made to contacting, it is meant to include all methods and mediums, including all phases of matter, in which the organic substrate and/or catalyst and/or deuterium or tritium source are brought either together or in such proximity to one another such that the catalyst of this invention may have a catalytic effect.

When reference is made to medium, it is meant the solvent of the process described herein. The solvent of the process described herein is generally water or $D_2O$. However, a solvent mixture of $D_2O$ and $CD_3CO_2D$ is also within the range of instant invention. Thus it is clear that this process can be run at a pH of between about 1 and 7, depending on the solvent used.

When reference is made to "contribute 6 electrons" it is to be known that the counting is done according to the ionic model it is meant that there are 6 electrons in the bond between the ligand and metal. The same meaning is attached to the phrase "6 electron donor". The same meaning is attached to the phrase "contribute 2 electrons" or "2 electron donor", except of course with a different number of electrons.

When reference is made to a polar solvent, polarity is measured by the standard method and the dielectric constant epsilon is greater than 20. Water has an epsilon value of 78.

When reference is made to deuterium labeled compounds or tritium labeled compounds, it is meant a compound having at least one ordinary H atom substituted with deuterium or tritium. Deuterium is an isotope of H whose nucleus contains a proton and a neutron. The symbol D may be used for deuterium and $D_2O$ may be referred to as deuterium oxide or heavy water, and can be obtained by electrolysis of ordinary water. Tritium is an isotope of H whose nucleus contains a proton and two neutrons. It is radioactive and is often given the symbol T. Deuterium labeled compound and tritium labeled compounds as referred to herein also includes coordination-sphere isomers, linkage isomers, geometrical isomers and optical isomers thereof.

When reference is made to the hydride ion, it is meant a H atom that has picked up one electron to form H⁻.

When reference is made to ligands, it is meant that to include broadly the molecules or ions that surround a metal ion in the catalyst complex. They may be monodentate or polydentate, be cations, anions or polar molecules, have any number of unshared valence electrons and participate in any type of bonding or coupling interaction. Ligand or ligands is also meant to include two species that may be fused or bonded or linked that cooperate to contribute to the coordination catalyst. An example of a catalyst using two species linked together is shown below:

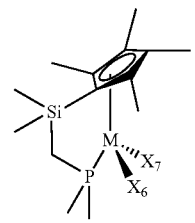

When reference is made to resistant to ligand redistribution, it is meant that $A_x$ and $L_x$, where x=1–6, are not labile, i.e. they do not dissociate from the metal during the catalytic process.

When reference is made to deuterium and deuteration it is intended to include also tritium and tritiation, or a mixture of deuterium and tritium.

When reference is made to substrate or organic substrate, it is meant the organic compound that is subject to deuteration and/or tritiation.

When reference is made to system, it is meant to include the functional catalyst as it is being used in the process claimed herein.

The structures of these transition metal complexes are further described below. The first complex, a type I complex, and represented for illustration purposes by, $Cp*(PMe_3)IrCl_2$, is a charge neutral complex, in the sense that the three "anionic" groups (the Cp* and two chloride ligands) are covalently bonded to the iridium center. That is, they are within the inner coordination sphere of the transition metal. While not wishing to be bound by any particular theory, it is believed that the mechanism of action of this catalyst on the organic substrate proceeds by dissociation of a chloride ligand to produce a cationic iridium center, $[Cp*(PMe_3)IrCl][Cl]$ with an outer-sphere chloride ligand. So, it is believed the active species to be an iridium (III) cation, and that the polar nature of the medium is critical to the catalyst's success.

Electronically, this complex may be described as having 18 electrons, which may be distributed to the various constituents, (the ionic counting method). Ionic counting convention requires that ligands are anionic or cationic and that the oxidation state of the metal is appropriate for the realistic distribution of electrons. In the ionic counting scheme, the iridium is said to be oxidized by the Cp* and 2 chloride ligands, and is therefore iridium (III), carrying 6 d electrons. The Cp* therefore donates 6, the two chlorides donate two apiece, and the phosphine (L type ligand) donates 2, giving a total of 18 electrons. This is because when the Cl dissociates, it dissociates as a chloride.

Note that the mechanism of action of the type I and II catalysts is believed to be the same. While not wishing to be bound by any particular theory, it is believed that the salt-like species $[Cp*(PMe_3)IrH_3][OTf]$, the type II complex, by illustration, is composed of discrete cations and anions, but the degree of association of these ions will of course be solvent dependent. That is, the more polar the solvent, the more the ions are dissociated. Electronically, this complex also has 18 electrons, and in the ionic counting scheme we have an iridium (V) species, having 4 d electrons. Each hydride ligand donates 2 electrons, the Cp* donates 6 electrons, the phosphine donates 2 electrons, and there is an overall positive charge on the complex. It appears that the mechanism of this catalyst begins with dihydrogen elimination to give an iridium (III) cation, [Cp*(PMe$_3$)IrH] [OTf].

Mechanistically, the type I and II catalysts are assumed to form a 16 electron catalytically active species, by either dissociating a ligand (ionizing in the case of type I) or reductively eliminating a ligand (a small molecule such as dihydrogen, in the case of type II).

Any organic or organometallic compound can be used as an organic substrate to be deuterated or tritiated by the catalysts of the present invention. Preferred examples of organic compounds include aliphatic compounds, alicyclic compounds, aromatic hydrocarbons and polymeric compounds such as plastics, rubbers and proteins. Specific examples of the alicyclic compounds include cyclohexane, methyl cyclohexane, pyridine and tetrahydrofuran. Specific examples of the aromatic hydrocarbons include benzene, toluene, ethylbenzene, xylene, bromobenzene, chlorobenzene, dichlorobenzene, nitrobenzene, phenol, hydroquinone, benzoic acid, salicylic acid, phthalic acid and aniline.

Preferably the catalysts according to the instant invention are organometallic in nature; the most active have been found to be [Cp*(PMe$_3$)IrH$_3$][OTf] and Cp*(PMe$_3$) IrCl$_2$, where Cp* is pentamethylcyclopentadienide, Me$_3$ is trimethyl and OTf is OSO$_2$CF$_3$. The latter catalyst is air stable, and is prepared in two high-yielding steps from commercially available IrCl$_3$-3H$_2$O.

The type I–VI catalysts described by this invention can be prepared according to methods known in the art. For example, Cp*(PMe$_3$) IrCl$_2$ can be prepared according to the methods described in J. C. S. Dalton Trans., pp. 2003–8, (1981) and hereby incorporated by reference in its entirety. [Cp*(PMe$_3$)IrH$_3$][OTf] can be prepared according to the methods described in Organometallics, 1992, 11, 231–237 and hereby incorporated by reference in its entirety. Other synthetic routes are disclosed in J. Am. Chem. Soc. 1997, 119, 11028–11036, "Synthesis and Characterization of Hydrotris(pyrazolyl)borate Dihydrogen/Hydride Complexes of Rhodium and Iridium". This reference is hereby incorporated by reference in its entirety.

The temperature that the deuteration and/or tritiation is accomplished can be anywhere in the range of from 75 to 200 degrees centigrade. Preferably the temperature is about 100–150 and more preferably the temperature is between about 130–140° C.

A typical method of deuterating is described next. The reaction scheme is shown below.

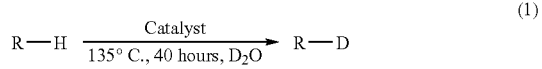

(1)

R represents any organic molecule. A J. Young-style NMR tube was charged with a type I catalyst, Cp*(PMe$_3$)IrCl$_2$, an organic substrate, D$_2$O (0.5 mL), and an external standard capillary (vide infra) consisting of 1,3,5-trimethoxybenzene dissolved in C$_6$D$_6$. The tube was then closed, and reaction progress was monitored by $^1$H NMR spectroscopy through loss of intensity of the organic substrate resonances. The deuteration level is calculated by dividing the standardized integration of the starting organic compound before heating by the measured standardized integration after heating at 135° C. first at 18 h and then at 40 h. $^2$H NMR spectroscopy was used as a qualitative tool to demonstrate the presence of deuterium in the incorporation for the substrate sodium octanoate were further confirmed by isolating the corresponding acid after acidic workup and extraction into diethyl ether (80% recovery) and checking the $^1$H NMR integrations against the internal standard 1,3,5-trimethoxybenzene. The process is completed when one or more deuterium atoms exchanges with one or more protons of the organic substrate molecule. The now deuterium-tagged organic molecule can be separated or isolated by techniques readily available to one of ordinary skill in the art. Methods and results for determining the amount of deuteration or tritiation are fully described in J. Am. Chem. Soc. 124, 2092–2093, the contents of which are hereby incorporated by reference in their entirety.

The external standard capillaries were prepared by first flame sealing one end of a 9-inch Pasteur pipette. The pipette was then filled to a level of approximately 5 cm with a solution prepared from approximately 200 mg 1,3,5-trimethoxybenzene and 2 mL C$_6$D$_6$. The capillaries were then sealed under partial vacuum with the aid of a pipette bulb. Because no exchange was observed to occur at room temperature, the samples containing these capillaries could be calibrated by $^1$H NMR spectroscopy before heating. The deuteration levels for the substrates reported herein were shown to be reproducible to within 5–10% by this method. For an example of NMR spectroscopy as a method of determining deuterium incorporation, see Lenges, C. P.: White, P. S.; Brookhart, M. J. Am. Chem. Soc. 1999, 121, 346, the contents of which are hereby incorporated by reference in their entirety.

The present invention will be described in detail with reference to the following Examples, but the invention should not be construed as being limited thereto.

EXAMPLE 1

A glass vessel was charged with 6.0 mg (0.013 mmol) Cp*(PMe$_3$)IrCl$_2$, 0.500 mL (27.6 mmol) D$_2$O, and 20 μL (0.247 mmol) tetrahydrofuran (THF), and an external standard capillary consisting of 1,3,5-trimethoxybenzene dissolved in C$_6$D$_6$. The vessel was sealed and the reaction mixture was heated to 135° C. for 43 h. Using $^1$H NMR spectroscopy, it was determined that the α-position of THF had been deuterium labeled to the extent of 89%, and the β-position had been labeled to the extent of 40%. The labeled tetrahydrofuran may be separated from the water by extraction with diethyl ether solvent. Distillation will enable the isolation of the pure labeled tetrahydrofuran. It was found that performing this procedure under a nitrogen atmosphere and an air atmosphere led to identical deuterium incorporation results.

EXAMPLE 2

A glass vessel was charged with 3.2 mg (0.0068 mmol) Cp*(PMe$_3$)IrCl$_2$, 0.500 mL (27.6 mmol) D$_2$O, and 14.2 μL (0.135 mmol) diethyl ether, and an external standard capillary consisting of 1,3,5-trimethoxybenzene dissolved in C$_6$D$_6$. The vessel was sealed and the reaction mixture was heated to 135° C. for 50 h. Using $^1$H NMR spectroscopy, it was determined that the α-position of diethyl ether had been deuterium labeled to the extent of 16%, and the β-position had been labeled to the extent of 55%. Distillation would enable isolation of the pure labeled diethyl ether.

EXAMPLE 3

A glass vessel was charged with 4.7 mg (0.0085 mmol) [Cp*(PMe$_3$)IrH$_3$][OTf], 0.500 mL (27.6 mmol) D$_2$O, and 20.7 mg (0.169 mmol) benzoic acid. The vessel was sealed and the reaction mixture was heated to 135° C. for 40 h. The reaction mixture within the vessel was then extracted with 3×2 mL diethyl ether and filtered through silica gel. Mass spectrometric analysis of the resulting solution indicated that the overall deuterium incorporation for the H/D exchange process was 80%.

EXAMPLE 4

A glass vessel was charged with 6.1 mg (0.011 mmol) [Cp*(PMe$_3$)IrH$_3$][OTf], 0.500 mL (27.6 mmol) D$_2$O, and 20 μL (0.173 mmol) tetrahydrofuran (THF). The vessel was sealed and the reaction mixture was heated to 135° C. for 48 h. Using $^1$H NMR spectroscopy, it was determined that the α-position of THF had been deuterium labeled to the extent of 86%, and the β-position had been labeled to the extent of 35%. The labeled tetrahydrofuran was separated from the water by extraction with diethyl ether solvent.

EXAMPLE 5

A glass vessel was charged with 5.0 mg (0.0067 mmol) [Cp*(PPh$_3$)IrH$_3$][OTf], 0.500 mL (27.6 mmol) D$_2$O, and 20 μL (0.173 mmol) tetrahydrofuran (THF). The vessel was sealed and the reaction mixture was heated to 135° C. for 4 h. Using $^1$H NMR spectroscopy, it was determined that the α-position of THF had been deuterium labeled to the extent of 25%, and the β-position had been labeled to the extent of 22%.

EXAMPLE 6

A glass vessel was charged with 6.1 mg (0.0087 mmol) Cp*(PMe$_3$)Ir(OTf)$_2$, 0.500 mL (27.6 mmol) D$_2$O, and 20 μL (0.247 mmol) tetrahydrofuran (THF), and an external standard capillary consisting of 1,3,5-trimethoxybenzene dissolved in C$_6$D$_6$. The vessel was sealed and the reaction mixture was heated to 135° C. for 59 h. Using $^1$H NMR spectroscopy, it was determined that the α-position of THF had been deuterium labeled to the extent of 63%, and the β-position had been labeled to the extent of 30%.

EXAMPLE 7

A glass vessel was charged with 5.3 mg (0.0095 mmol) [Cp*(PMe$_3$)IrH$_3$][OTf], 0.250 mL (27.6 mmol) D$_2$O, 0.250 mL CD$_3$CO$_2$D, and 20 μL (0.173 mmol) tetrahydrofuran (THF). The vessel was sealed and the reaction mixture was heated to 135° C. for 14 h. Using $^1$H NMR spectroscopy, it was determined that the α-position of THF had been deuterium labeled to the extent of 94%, and the β-position had been labeled to the extent of 40%.

EXAMPLE 8

A glass vessel was charged with 6.4 mg (0.013 mmol) Cp*(PMe$_3$)IrBr$_2$, 0.500 mL (27.6 mmol) D$_2$O, and 17 μL (0.227 mmol) n-propanol, and an external standard capillary consisting of 1,3,5-trimethoxybenzene dissolved in C$_6$D$_6$. The vessel was sealed and the reaction mixture was heated to 135° C. for 40 h. Using $^1$H NMR spectroscopy, it was determined that the α-position had been deuterium labeled to the extent of 58%, the α-position had been labeled to the extent of 39%, and the γ-position had been labeled to the extent of 60%. The labeled n-propanol was separated from the water by extraction with diethyl ether solvent.

EXAMPLE 9

A glass vessel was charged with 6.9 mg (0.014 mmol) [Cp*(PMe$_3$)Ir(OH$_2$)$_2$][SO$_4$], 0.500 mL (27.6 mmol) D$_2$O, and 14.2 μL (0.135 mmol) diethyl ether, and an external standard capillary consisting of 1,3,5-trimethoxybenzene dissolved in C$_6$D$_6$. The vessel was sealed and the reaction mixture was heated to 135° C. for 42 h. Using $^1$H NMR spectroscopy, it was determined that the α-position of diethyl ether had been deuterium labeled to the extent of 29%, and the β-position had been labeled to the extent of 72%.

EXAMPLE 10

A glass vessel was charged with 6.9 mg (0.014 mmol) ($\eta^5$:$\eta^1$-(Me$_2$P(CH$_2$SiMe$_2$)C$_5$Me$_4$)Ir(OSO$_2$CF$_3$)$_2$, 0.500 mL (27.6 mmol) D$_2$O, and 20.6 μL (0.196 mmol) diethyl ether, and an external standard capillary consisting of 1,3,5-trimethoxybenzene dissolved in C$_6$D$_6$. The vessel was sealed and the reaction mixture was heated to 135° C. for 40 h. Using $^1$H NMR spectroscopy, it was determined that the α-position of diethyl ether had been deuterium labeled to the extent of 19%, and the β-position had been labeled to the extent of 42%.

EXAMPLE 11

A glass vessel was charged with 5.7 mg (0.0099 mmol) [($\eta^5$:$\eta^1$-(Me$_2$P(CH$_2$SiMe$_2$)C$_5$Me$_4$)Ir(OH$_2$)$_2$][SO$_4$], 0.500 mL (27.6 mmol) D$_2$O, and 20.7 μL (0.197 mmol) diethyl ether, and an external standard capillary consisting of 1,3,5-trimethoxybenzene dissolved in C$_6$D$_6$. The vessel was sealed and the reaction mixture was heated to 135° C. for 40 h. Using $^1$H NMR spectroscopy, it was determined that the α-position of diethyl ether had been deuterium labeled to the extent of 31%, and the β-position had been labeled to the extent of 46%.

EXAMPLE 12

A glass vessel was charged with 14.6 mg (0.034 mmol) Cp*(NH$_2$$^t$Bu)IrCl$_2$, 0.500 mL (27.6 mmol) D$_2$O, and 70.5 μL (0.672 mmol) diethyl ether, and an external standard capillary consisting of 1,3,5-trimethoxybenzene dissolved in C$_6$D$_6$. The vessel was sealed and the reaction mixture was heated to 135° C. for 40 h. Using $^1$H NMR spectroscopy, it was determined that the overall deuterium incorporation for diethyl ether was 25%.

EXAMPLE 13

A glass vessel was charged with 5.2 mg (0.011 mmol) Cp*(PF$_3$)IrCl$_2$, 0.500 mL (27.6 mmol) D$_2$O, and 50.0 μL (0.428 mmol) diethyl ether, and an external standard capillary consisting of 1,3,5-trimethoxybenzene dissolved in C$_6$D$_6$. The vessel was sealed and the reaction mixture was heated to 135° C. for 40 h. Using ¹H NMR spectroscopy, it was determined that the overall deuterium incorporation for diethyl ether was 14%.

EXAMPLE 14

A glass vessel was charged with 7.5 mg (0.016 mmol) Cp*(PMe₃)IrCl₂, 0.500 mL (27.6 mmol) D₂O, 15.4 mg (0.0789 mmol) YCl₃, and 23.6 µL (0.316 mmol) n-propanol, and an external standard capillary consisting of 1,3,5-trimethoxybenzene dissolved in C₆D₆. The vessel was sealed and the reaction mixture was heated to 135° C. for 40 h. Using ¹H NMR spectroscopy, it was determined that the α-position had been deuterium labeled to the extent of 35%, the β-position had been labeled to the extent of 29%, and the γ-position had been labeled to the extent of 29%. The labeled n-propanol was separated from the water by extraction with diethyl ether solvent.

EXAMPLE 15

A glass vessel was charged with 9.0 mg (0.012 mmol) Tp$^{Me2}$(PMe₃)IrBr₂(Tp$^{Me2}$=hydridotris(3,5-dimethylpyrazolyl)borate), 0.500 mL (27.6 mmol) D₂O, and 18.6 µL (0.248 mmol) n-propanol, and an external standard capillary consisting of 1,3,5-trimethoxybenzene dissolved in C₆D₆. The vessel was sealed and the reaction mixture was heated to 135° C. for 40 h. Using ¹H NMR spectroscopy, it was determined that the α-position had been deuterium labeled to the extent of 40%, the β-position had been labeled to the extent of 39%, and the γ-position had been labeled to the extent of 58%. The labeled n-propanol was separated from the water by extraction with diethyl ether solvent.

Although the foregoing invention has been described in some detail for purposes of clarity of understanding, those skilled in the art will appreciate that various adaptations and modifications of the just described preferred embodiments can be configured without departing from the scope and spirit of the invention. Therefore, the described embodiments should be taken as illustrative and not restrictive, and the invention should not be limited to the details given herein but should be defined by the following claims and their full scope of equivalents.

We claim:

1. A method of preparing a deuterium labeled or tritium labeled compound comprising contacting an organic substrate with a catalyst having at least one of the following structures:

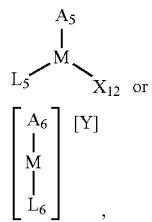

where M is selected from the group consisting of Ni, Pd and Pt;

A₅ and A₆ each independently represent ligands that are a 6 electron donor;

L₅ and L₆ each independently represent ligands that are a 2 electron donor;

X₁₂ represents ligands that are a two electron donors;

Y is an anion capable of creating a charge neutral complex, and contacting the organic substrate and said catalyst with a source of deuterium or tritium and heating the combination at a temperature of from 75–200° C.

2. A method of preparing a deuterium labeled or tritium labeled compound according to claim 1, where A₅ and A₆ are pentamethylcyclopentadienide.

3. A method of preparing a deuterium labeled or tritium labeled compound according to claim 1, wherein the source of deuterium is D₂O.

4. A method of preparing a deuterium labeled or tritium labeled compound according to claim 1, wherein the source of tritium is T₂O.

5. A method of preparing a deuterium labeled or tritium labeled compound according to claim 1, wherein the combination is heated at a temperature of from 100–150° C.

6. A method of preparing a deuterium labeled or tritium labeled compound according to claim 1, wherein the combination is heated at a temperature of from 130–140° C.

7. A method of preparing a deuterium labeled or tritium labeled compound according to claim 1, wherein said catalyst is resistant to ligand redistribution.

* * * * *

UNITED STATES PATENT AND TRADEMARK OFFICE
CERTIFICATE OF CORRECTION

| | | |
|---|---|---|
| PATENT NO. | : 7,057,055 B2 | Page 1 of 1 |
| APPLICATION NO. | : 11/243852 | |
| DATED | : June 6, 2006 | |
| INVENTOR(S) | : Robert G. Bergman and Steven R. Klei | |

It is certified that error appears in the above-identified patent and that said Letters Patent is hereby corrected as shown below:

Inventor's name "Robert C. Bergman" should be --Robert G. Bergman--.

Signed and Sealed this

Twenty-second Day of August, 2006

JON W. DUDAS
*Director of the United States Patent and Trademark Office*